US011806507B2

(12) United States Patent
Herzlinger

(10) Patent No.: US 11,806,507 B2
(45) Date of Patent: Nov. 7, 2023

(54) METHODS, SYSTEMS, AND APPARATUS FOR ADMINISTERING AN ANTIBODY TREATMENT VIA INFUSION

(71) Applicant: Regina E. Herzlinger, Belmont, MA (US)

(72) Inventor: Regina E. Herzlinger, Belmont, MA (US)

( * ) Notice: Subject to any disclaimer, the term of this patent is extended or adjusted under 35 U.S.C. 154(b) by 0 days.

(21) Appl. No.: 17/840,423

(22) Filed: Jun. 14, 2022

(65) Prior Publication Data

US 2022/0379026 A1 Dec. 1, 2022

Related U.S. Application Data

(63) Continuation-in-part of application No. 17/558,295, filed on Dec. 21, 2021.

(60) Provisional application No. 63/343,963, filed on May 19, 2022, provisional application No. 63/341,928, filed on May 13, 2022, provisional application No. 63/286,353, filed on Dec. 6, 2021, provisional application No. 63/280,953, filed on Nov. 18, 2021, provisional application No. 63/253,790, filed on Oct. 8, 2021, provisional application No. 63/249,299, filed on Sep. 28, 2021, provisional application No.
(Continued)

(51) Int. Cl.
*A61M 5/168* (2006.01)
*A61M 5/142* (2006.01)
*A61M 5/158* (2006.01)
*A61M 5/165* (2006.01)

(52) U.S. Cl.
CPC ........ *A61M 5/16881* (2013.01); *A61M 5/142* (2013.01); *A61M 2005/1587* (2013.01); *A61M 2005/1657* (2013.01)

(58) Field of Classification Search
CPC .. A61K 39/00; A61K 39/395; A61K 39/3955; A61M 5/002; A61M 5/1413; A61M 5/14244; A61M 5/152; A61M 5/162; A61M 5/165; A61M 5/16813; A61M 5/16881; A61M 5/14; A61M 5/142; A61M 5/145; A61M 5/148; A61M 5/16804; A61M 5/168; A61M 5/16877
See application file for complete search history.

(56) References Cited

U.S. PATENT DOCUMENTS 5,319,170 A 6/1994 Cassidy
5,366,346 A 11/1994 Danby
(Continued)

FOREIGN PATENT DOCUMENTS

WO WO-2020/084375 A1 4/2020
WO WO-2022/140463 A1 6/2022

OTHER PUBLICATIONS

AIS Health, Rezurock is approved with more transplant agents in pipeline, Member: Radar on Drug Benefits, 8 pages, (Jul. 22, 2021).
(Continued)

*Primary Examiner* — Jason E Flick
(74) *Attorney, Agent, or Firm* — William R. Haulbrook; Peter A. Flynn; Samuel E. Bliesner

(57) ABSTRACT

Presented herein are methods, systems, and apparatus for administering an antibody treatment via an infusion device, e.g., a rapid infusion device, e.g., for the treatment of a disease or condition that requires one or more infusions of monoclonal and/or polyclonal antibodies.

18 Claims, 4 Drawing Sheets

Related U.S. Application Data

63/227,803, filed on Jul. 30, 2021, provisional application No. 63/223,921, filed on Jul. 20, 2021, provisional application No. 63/220,854, filed on Jul. 12, 2021, provisional application No. 63/129,401, filed on Dec. 22, 2020.

(56) References Cited

U.S. PATENT DOCUMENTS

| | | | |
|---|---|---|---|
| 6,175,688 | B1 | 1/2001 | Cassidy et al. |
| 6,236,809 | B1 | 5/2001 | Cassidy et al. |
| 6,480,257 | B2 | 11/2002 | Cassidy et al. |
| 7,819,875 | B2 | 10/2010 | Chana |
| 9,737,672 | B2 | 8/2017 | Landy et al. |
| 10,293,099 | B2 | 5/2019 | Woolford |
| 10,485,936 | B2 | 11/2019 | Landy, III et al. |
| 10,822,379 | B1 | 11/2020 | Dimitrov et al. |
| 10,995,137 | B2 | 5/2021 | Pedersen et al. |
| 2002/0016570 | A1* | 2/2002 | Cartledge ............ A61M 5/142 604/131 |
| 2004/0009216 | A1 | 1/2004 | Rodrigueza et al. |
| 2009/0162353 | A1 | 6/2009 | Johnson et al. |
| 2009/0192446 | A1 | 7/2009 | Landy, III et al. |
| 2013/0216742 | A1 | 8/2013 | DeMartino et al. |
| 2016/0355589 | A1* | 12/2016 | Williams .............. A61P 35/00 |
| 2021/0246226 | A1 | 8/2021 | Baum et al. |
| 2021/0284732 | A1* | 9/2021 | Zugmaier .......... C07K 16/2878 |
| 2022/0088075 | A1* | 3/2022 | O'Rourke .......... C07K 16/2818 |
| 2022/0193235 | A1 | 6/2022 | Herzlinger |
| 2022/0193236 | A1 | 6/2022 | Herzlinger |

OTHER PUBLICATIONS

Anderson, T.S. et al., Uptake of Outpatient Monoclonal Antibody Treatments for COVID-19 in the United States: a Cross-Sectional Analysis, J Gen. Intern. Med., 36(12):3922-3924 (2021).

Atmar, J., Review of the Safety and Feasibility of Rapid Infusion of Rituximab, Journal of Oncology Practice, 6(2):91-93 (2010).

Bariola, J.R. et al., Impact of Bamlanivimab Monoclonal Antibody Treatment on Hospitalization and Mortality Among Nonhospitalized Adults With Severe Acute Respiratory Syndrome Coronavirus 2 Infection, Open Forum Infectious Diseases, 8(7):ofab254 (2021).

Barnard, J.G. et al., Subvisible particle counting provides a sensitive method of detecting and quantifying aggregation of monoclonal antibody caused by freeze-thawing: insights into the roles of particles in the protein aggregation pathway, J. Pharm. Sci., 100(2):492-503 (2011).

Berrill, A. et al., Product quality during manufacture and supply, Peptide and Protein Delivery, Academic Press, pp. 313-339, (2011).

Bozzette, S.A. et al., Cardiovascular and cerebrovascular events in patients treated for human immunodeficiency virus infection. N. Engl. J. Med., 348(8):702-710 (2003).

Bril, V. et al., Efficacy and Safety of Rozanolixizumab in Moderate to Severe Generalized Myasthenia Gravis: A Phase 2 Randomized Control Trial, Neurology, 96(6):e853-e865 (2021).

Buntz, B., 50 of 2020's best-selling pharmaceuticals, Drug Discovery and Development, 6 pages, (May 14, 2021), retrieved online at: https://www.drugdiscoverytrends.com/50-of-2020s-best-selling-pharmaceuticals/.

Castaneda, R., Oral Covid-19 drugs: Merck's molnupiravir and its closest rivals, Clinical Trials Arena, 12 pages, (2021), retrieved online at: https://www.clinicaltrialsarena.com/analysis/oral-covid-19-drugs-molnupiravir/.

Centers for Medicare and Medicaid Services, CMS Increases Medicare Payment for COVID-19 Monoclonal Antibody Infusions, 2 pages, (2021), retrieved online at: https://www.cms.gov/newsroom/press-releases/cms-increases-medicare-payment-covid-19-monoclonal-antibody-infusions.

Chi, E.Y., et al., Physical stability of proteins in aqueous solution: mechanism and driving forces in nonnative protein aggregation, Pharm. Res., 20(9):1325-1336 (2003).

clinicaltrials.gov, A Study to Evaluate Safety, Tolerability, and Efficacy of Lecanemab in Subjects with Early Alzheimer's Disease, 11 pages, (2020), retrieved online at: https://clinicaltrials.gov/ct2/show/NCT01767311.

Cohen, M.S. et al. Effect of Bamlanivimab vs Placebo on Incidence of COVID-19 Among Residents and Staff of Skilled Nursing and Assisted Living Facilities: A Randomized Clinical Trial, JAMA, 326(1):46-55 (2021).

Creative Biolabs Therapeutics, Antibody Stability Analysis, (2022), retrieved online at: https://www.creative-biolabs.com/drug-discovery/therapeutics/antibody-stability-analysis.htm.

Creative Biolabs Therapeutics, C-Terminal Lysine Variant Analysis, 5 pages, (2022), retrieved online at: https://www.creative-biolabs.com/drug-discovery/therapeutics/c-terminal-lysine-variant-analysis.htm.

Creative Biolabs Therapeutics, Dynamic Light Scattering (DLS), 5 pages, (2022), retrieved online at: https://www.creative-biolabs.com/drug-discovery/therapeutics/dynamic-light-scattering-dls.htm.

Creative Biolabs Therapeutics, N-Terminal Cyclization Analysis, 5 pages, (2022), retrieved online at: https://www.creative-biolabs.com/drug-discovery/therapeutics/n-terminal-cyclization-analysis.htm.

Creative Biolabs Therapeutics, Oxidation Analysis, 5 pages, (2022), retrieved online at: https://www.creative-biolabs.com/drug-discovery/therapeutics/oxidation-analysis.htm.

Creative Biolabs Therapeutics, Sedimentation Velocity Analytical Ultracentrifugation (SV-AUC) for Antibody Aggregation Analysis, 5 pages, (2022), retrieved online at: https://www.creative-biolabs.com/drug discovery/therapeutics/sedimentation-velocity-analytical-ultracentrifugation-sv-auc-for-antibody-aggregation-analysis.htm.

Creative Biolabs Therapeutics, Size Exclusion Chromatography (SEC) for Antibody Aggregation Analysis, 5 pages, (2022), retreived online at: https://www.creative-biolabs.com/drug-discovery/therapeutics/size-exclusion-chromatography-sec-for-antibody-aggregation-analysis.htm.

Dirks, N.L. and Meibohm, B., Population pharmacokinetics of therapeutic monoclonal antibodies. Clin. Pharamcokinet., 49:633-659 (2010).

Dostalek, M. et al., Pharmacokinetics, pharmacodynamics and physiologically-based pharmacokinetic modelling of monoclonal antibodies, Clin. Pharmacokinet., 52:83-124 (2013).

Duan, T. et al., Affinity-matured 'aquaporumab' anti-aquaporin-4 antibody for therapy of seropositive neuromyelitis optica spectrum disorders, Neuropharmacology, 162:107827 (2019).

Dunleavy, K., Regeneron, GlaxoSmithKline and Eli Lilly COVID-19 drugs prioritized for expedited review, 3 pages, (Jun. 30, 2021), retrieved online at: https://www.fiercepharma.com/pharma/covid-19-treatments-from-regeneron-lilly-gsk-vir-among-5-prioritized-for-expedited-review.

Eli Lilly, Emergency Use Authorization (EUA) for the Treatment or Post-Exposure Prophylaxis of COVID-19, 2 pages, (2021), retrieved online at: https://www.covid19.lilly.com/bamlanivimab/hcp/dosing-administration.

European Commission, Questions and Answers: COVID-19 Therapeutics Strategy—list of 5 candidate therapeutics, 4 pages, (2021), retrieved online at: https://ec.europa.eu/commission/presscorner/detail/en/qanda_21_3301.

Eviq, Infusion related reaction, NSW Government, 1 page, (2017), retrieved online at: https://www.eviq.org.au/dose-mod-gradings/standard-ctcae/infusion-related-reaction-irr.

Franklin, B.D., 'Smart' intravenous pumps: how smart are they?, BMJ Qual. Saf., 26:93-94 (2017).

Gaudinski M.R. et al., Safety, tolerability, pharmacokinetics, and immunogenicity of the therapeutic monoclonal antibody mAb114 targeting Ebola virus glycoprotein (VRC 608): an open-label phase 1 study, Lancet, 393(10174):889-898 (2019).

Gedeon, P.C. et al., GLP toxicology study of a fully-human T cell redirecting CD3:EGFRvIII binding immunotherapeutic bispecific antibody. PLoS One, 15:e0236374 (2020).

Genentech, Inc., A Study of Rituximab Alternative Dosing Rate in Patients With Previously Untreated Diffuse Large B-cell or Follicular Non-Hodgkin's Lymphoma (RATE) (RATE), 8 pages, (2017), U.S. National Library of Medicine, retrieved online at: https://clinicaltrials.gov/ct2/show/study/NCT00719472.

(56) References Cited

OTHER PUBLICATIONS

Genentech, Inc., Fact Sheet For Healthcare Providers: Emergency Use Authorization For Actemra® (tocilizumab), 18 pages, (2021), retrieved online at: https://www.fda.gov/media/150321/download.
Genentech, Inc., Rituxan Dosing and Administration, 7 pages, (2022), retrieved online at: https://www.rituxan-hcp.com/nhl-cll/dosing-and-administration/rituxan-administration/rituxan-infusion.html.
Genentech, Inc., Rituxan, 5 pages, (2022), retrieved online at: rituxan-hcp.com.
Genzyme Polyclonals S.A.S., Thymoglobulin Highlights of Prescribing Information, 6 pages, (2020), retrieved online at: https://products.sanofi.us/thymoglobulin/thymoglobulin.pdf.
Gklinos, P. et al., Monoclonal Antibodies as Neurological Therapeutics, Pharmaceuticals, 14(2):92 (2021).
Glaxosmithkline, LLC, Fact Sheet For Healthcare Providers Emergency Use Authorization (Eua) Of Sotrovimab, 32 pages, (2022), retrieved online at: https://www.fda.gov/media/149534/download.
Glaxosmithkline, Primary endpoint met in COMET-TAIL Phase III trial evaluating intramuscular administration of sotrovimab for early treatment of COVID-19, 16 pages, (2021), retrieved online at: https://www.gsk.com/en-gb/media/press-releases/primary-endpoint-met-in-comet-tail-phase-iii-trial-evaluating-intramuscular-administration-of-sotrovimab-for-early-treatment-of-covid-19/.
Gupta, A. et al., Early Treatment for Covid-19 with SARS-CoV-2 Neutralizing Antibody Sotrovimab, N. Engl. J. Med., 385(21):1941-1950 (2021).
Harn, N. et al., Highly concentrated monoclonal antibody solutions: direct analysis of physical structure and thermal stability, J. Pharm. Sci., 96(3):532-546 (2007).
Hauptmann, A. et al., Impact of buffer, protein concentration and sucrose addition on the aggregation and particle formation during freezing and thawing, Pharm. Res., 35(5):101 (2018).
Hawe, A. et al., Structural properties of monoclonal antibody aggregates induced by freeze-thawing and thermal stress, Eur. J. Pharm. Sci., 38(2):79-87 (2009).
Herzlinger, B. and Richman, B., Preparing Hospitals for the Next Pandemic, Harvard Business Review, 6 pages, (2021), retrieved online at: https://hbr.org/2021/06/preparing-hospitals-for-the-next-pandemic.
Horn, J. et al., Impact of fast and conservative freeze-drying on product quality of protein-mannitol-sucrose-glycerol lyophilizates, Eur. J. Pharm. Biopharm., 127:342-354 (2018).
Hospimedica International, European Commission Identifies 10 Most Promising Treatments for COVID-19, 2 pages, (Oct. 26, 2021), retrieved online at: https://www.hospimedica.com/covid-19/articles/294790274/european-commission-identifies-10-most-promising-treatments-for-covid-19.html.
Hruz, P.W., HIV protease inhibitors and insulin resistance: lessons from in-vitro, rodent and healthy human volunteer models. Curr. Opin. HIV AIDS, 3(6):660-665 (2008).
International Search Report for PCT/US21/64724, filed Dec. 21, 2021, 4 pages, (May 18, 2022).
Kamath, E.D. et al., Translational pharmacokinetics and pharmacodynamics of monoclonal antibodies, Drug Discov. Today Technol., 21-22:75-83 (2016).
Katella, K., 9 Things You Need to Know About the New COVID-19 Pill, Yale Medicine, 5 pages, (2021), retrieved online at: https://www.yalemedicine.org/news/9-things-to-know-about-covid-pill.
Keizer, R.J. et al., Clinical pharmacokinetics of therapeutic monoclonal antibodies, Clin. Pharmacokinet., 49:493-507 (2010).
Kimball, S., FDA advisory panel narrowly endorses Merck's oral Covid treatment pill, despite reduced efficacy and safety questions, CNBC Health and Science, 7 pages, (2021), retrieved online at: Covid news: FDA panel narrowly endorses Merck pill, despite reduced efficacy (cnbc.com).
Kotler, D.P., HIV and antiretroviral therapy: lipid abnormalities and associated cardiovascular risk in HIV-infected patients. J. Acquir. Immune Defic. Syndr., 49(Suppl. 2):S79-S85 (2008).
Kueltzo, L.A. et al., Effects of solution conditions, processing parameters, and container materials on aggregation of a monoclonal antibody during freeze-thawing, J. Pharm. Sci., 97(5):1801-1812 (2008).
Le Basle, Y. et al., Physiochemical stability of monoclonal antibodies: a review, J. Pharm. Sci. 109:169-190 (2020).
Li, S. et al., Aggregation and precipitation of human relaxin induced by metal-catalyzed oxidation, Biochemistry, 34(17):5762-5772 (1995).
Lobo, E.D. et al., Antibody pharmacokinetics and pharmacodynamics, J. Pharm. Sci., 93:2645-2668 (2004).
Mahler, H.C. et al., Protein aggregation: pathways, induction factors and analysis, J Pharm Sci., 98(9):2909-2934 (2009).
Masato, A. et al., Suppression of Methionine Oxidation of a Pharmaceutical Antibody Stored in a Polymer-Based Syringe, J. Pharm. Sci., 105(2):623-629 (2016).
Mehta, S.B. et al., Gelation of a monoclonal antibody at the silicone oilewater interface and subsequent rupture of the interfacial gel results in aggregation and particle formation, J. Pharm. Sci., 104(4):1282-1290 (2015).
Merck and Co., Inc., Merck and Ridgeback's Investigational Oral Antiviral Molnupiravir Reduced the Risk of Hospitalization or Death by Approximately 50 Percent Compared to Placebo for Patients with Mild or Moderate COVID-19 in Positive Interim Analysis of Phase 3 Study, 8 pages, (2021), retrieved online at: https://www.merck.com/news/merck-and-ridgebacks-investigational-oral-antiviral-molnupiravir-reduced-the-risk-of-hospitalization-or-death-by-approximately-50-percent-compared-to-placebo-for-patients-with-mild-or-moderat/.
Minnema, L.A. et al., Exploring the Association between Monoclonal Antibodies and Depression and Suicidal Ideation and Behavior: A VigiBase Study, Drug Saf., 42(7):887-895 (2019).
Mita, A. C. et al., Phase I and pharmacokinetic study of AI-850, a novel microparticle hydrophobic drug delivery system for paclitaxel, Clin. Cancer Res., 13(11):3293-3301, (2007).
Munson, E.S., Air from IV bags may pose danger; venous embolism comes from many causes, APSF Newsletter, 8(2), 6 pages, (1993), retreived online at: https://www.apsf.org/article/air-from-iv-bags-may-pose-danger-venous-embolism-comes-from-many-causes/.
National Home Infusion Association, Home Infusion of Covid-19 Monoclonal Antibodies, 4 pages, (2021), retrieved online at: https://nhia.org/NEWS/BAM-PILOT-PROGRAM/.
National Infusion Center Association website, 9 pages, retrieved online at: https://infusioncenter.org.
NBC Channel 5 Chicago, What to Know About COVID-19 Pills and What They Mean for the Pandemic Fight, 6 pages, (2021), retrieved online at: https://www.nbcchicago.com/news/coronavirus/what-to-know-about-covid-19-pills-and-what-they-mean-for-the-pandemic-fight/2686151/.
Nicoud, L. et al., Kinetics of monoclonal antibody aggregation from dilute toward concentrated conditions, J. Phys. Chem. B. 120(13):3267-3280 (2016).
NIH COVID-19 Treatment Guidelines, Anti-SARS-CoV-2 Monoclonal Antibodies, 8 pages, (2022), retrieved online at: https://www.covid19treatmentguidelines.nih.gov/therapies/anti-sars-cov-2-antibody-products/anti-sars-cov-2-monoclonal-antibodies/.
Ogawa, C. et al., Analysis of inline-filter blockage with trastuzumab formulation using scanning-electron microscopy, Biomed. Pharmacother., 112:108711 (2019).
Osterberg, L. and Blaschke, T., Adherence to medication, N. Engl. J. Med., 353:487-497 (2005).
Pfizer Inc., Pfizer's Novel COVID-19 Oral Antiviral Treatment Candidate Reduced Risk of Hospitalization or Death by 89% in Interim Analysis of Phase 2/3 EPIC-HR Study, 8 pages, (2021), retrieved online at: https://www.pfizer.com/news/press-release/press-release-detail/pfizers-novel-covid-19-oral-antiviral-treatment-candidate.
Pfizer Injectables, Atgam Full Prescribing Information, 15 pages, (2021), retrieved online at: http://labeling.pfizer.com/ShowLabeling.aspx?id=525.
Regeneron Pharmaceuticals, Inc., COV-2067 Phase 3 Trial In High-Risk Outpatients Shows That Regen-Covtm (2400 Mg And 1200 Mg Iv Doses) Significantly Reduces Risk Of Hospitalization Or Death While Also Shortening Symptom Duration, 40 pages,

(56) References Cited

OTHER PUBLICATIONS (2021), retrieved online at: https://newsroom.regeneron.com/index.php/static-files/a7173b5a-28f3-45d4-bede-b97370bd03f8.
Regeneron Pharmaceuticals, Inc., Fact Sheet for Health Care Providers Emergency Use Authorization (EUA) of Regen-Cov® (casirivimab and imdevimab), 54 pages, (2022), retrieved online at: https://www.regeneron.com/downloads/treatment-covid19-eua-fact-sheet-for-hcp.pdf.
Regeneron Pharmaceuticals, Inc., Phase 3 Trial Shows Regen-Cov™ (Casirivimab With Imdevimab) Antibody Cocktail Reduced Hospitalization Or Death By 70% In Non-Hospitalized Covid-19 Patients, 7 pages, (2021), retrieved online at: https://investor.regeneron.com/news-releases/news-release-details/phase-3-trial-shows-regen-covtm-casirivimab-imdevimab-antibody.
Rivera, G. et al., Rapid implementation of pharmacy infusion services for emergency use authorization COVID-19 treatments at a field hospital, Am. J. Health Syst. Pharm., 78(22):2015-2019, (2021).
Rombouts, M.D. et al., Systematic Review on Infusion Reactions to and Infusion Rate of Monoclonal Antibodies Used in Cancer Treatment, Anticancer Research, 40(3):1201-1218 (2020).
Rosenberg, A.S., Effects of protein aggregates: am immunologic perspective, AAPS J., 8(3):E501-E507 (2006).
Ryman, J.T. and Meibohm, B., Pharmacokinetics and Monoclonal Antibodies, CPT Pharmacometrics Syst. Pharmacol., 6(9):576-588 (2017).
Salinas, B. et al., Understanding and modulating opalescence and viscosity in a monoclonal antibody formulation, J Pharm. Sci., 99(1):82-93 (2010).
Schermeyer, M.T. et al., Characterization of highly concentrated antibody solution—a toolbox for the description of protein long-term solution stability, MAbs, 9(7):1169-1185 (2017).
Schofield, D.J. et al., Preclinical development of a high affinity a-synuclein antibody, MEDI1341, that can enter the brain, sequester extracellular a-synuclein and attenuate a-synuclein spreading in vivo, Neurobiol. Dis., 132:104582 (2019).
Shire, S.J., Stability of monoclonal antibodies (mAbs), Monoclonal Antibodies, Woodhead Publishing, pp. 45-92, (2015).
Soontornniyomkij, V. et al., HIV protease inhibitor exposure predicts cerebral small vessel disease. AIDS. 28(9):1297-1306 (2014).
Sreedhara, A. et al., Stability of IgG1 monoclonal antibodies in intravenous infusion bags under clinical in-use conditions, J. Pharm. Sci., 101(1):21-30 (2012).
STAT Staff, Eight lingering questions about the new Covid pills from Merck and Pfizer, STAT Health, 10 pages, (2021), retrieved online at: https://www.statnews.com/2021/11/15/8-lingering-questions-about-the-new-covid-pills-from-merck-and-pfizer/.
Swan, J. T. et al., Use of a pharmacy protocol to convert standard rituximab infusions to rapid infusion shortens outpatient infusion clinic visits, Pharmacotherapy, 34(7):686-694, (2014).
The White House, National COVID-19 Preparedness Plan, 11 pages, (2022), retrieved online at: https://www.whitehouse.gov/covidplan/.
U.S. Department of Health and Human Services and U.S. Department of Defense, OWS Therapeutics Pre-EUA Playbook—Monoclonal Antibodies, Operation Warp Speed, 22 pages, (2020), retrieved online at: https://www.aha.org/system/files/media/file/2020/11/operation-warp-speed-playbook-allocation-distribution-covid-19-therapeutic-medications.pdf.
U.S. Department of Health and Human Services, Monoclonal Antibody Infusion Center Model (15 Stations), 4 pages, (2021), retrieved online at: https://www.phe.gov/emergency/events/COVID19/therapeutics/Pages/Infusion-Center-Model.aspx.
U.S. Food and Drug Administration, Emergency Use Authorization for Vaccines Explained, 3 pages, (2020), retrieved online at: https://www.fda.gov/vaccines-blood-biologics/vaccines/emergency-use-authorization-vaccines-explained.
U.S. Food and Drug Administration, Fact Sheet for Health Care Providers Emergency Use Authorization (EUA) of Bamlanivimab and Etesevimab, 45 pages, (2022), retrieved online at: https://www.fda.gov/media/145802/download.
U.S. Food and Drug Administration, Points to Consider in the Manufacture and Testing of Monoclonal Antibody Products for Human Use, 2 pages, (1997), retrieved online at: https://www.fda.gov/regulatory-information/search-fda-guidance-documents/points-consider-manufacture-and-testing-monoclonal-antibody-products-human-use.
Uchiyama, S., Liquid formulation for antibody drugs. Biochim. Biophys. Acta. 1844(11):2041-2052 (2014).
Wan, H., What ADME tests should be conducted for preclinical studies? ADMET and DMPK, 1(3):19-28 (2013).
Wang, M. et al., Interactions between biological products and product packaging and potential approaches to overcome them, AAPS PharmSciTech., 19(8):3681-3686 (2018).
Wang, W. et al., Monoclonal antibody pharmacokinetics and pharmacodynamics, Clin. Pharmacol. Ther., 84:548-558 (2008).
Wang, W., Protein aggregation and its inhibition in biopharmaceutics, Int. J. Pharm., 289(1-2):1-30 (2005).
Written Opinion for PCT/US21/64724, filed Dec. 21, 2021, 9 pages, (dated May 18, 2022).
Yang, R. et al., Rapid assessment of oxidation via middledown LCMS correlates with methionine side-chain solvent-accessible surface area for 121 clinical stage monoclonal antibodies, MAbs, 9(4):646-653 (2017).
Zhao L. et al., The antibody drug absorption following subcutaneous or intramuscular administration and its mathematical description by coupling physiologically based absorption process with the conventional compartment pharmacokinetic model, J. Clin. Pharmacol., 53:314-325 (2013).

\* cited by examiner

METHODS, SYSTEMS, AND APPARATUS FOR ADMINISTERING AN ANTIBODY TREATMENT VIA INFUSION

CROSS-REFERENCE TO RELATED APPLICATIONS

This application is a continuation-in-part of U.S. application Ser. No. 17/558,295 filed on Dec. 21, 2021, which claims the benefit of U.S. Provisional Application No. 63/129,401 filed on Dec. 22, 2020, U.S. Provisional Application No. 63/220,854 filed on Jul. 12, 2021, U.S. Provisional Application No. 63/223,921 filed on Jul. 20, 2021, U.S. Provisional Application No. 63/227,803 filed on Jul. 30, 2021, U.S. Provisional Application No. 63/249,299 filed on Sep. 28, 2021, U.S. Provisional Application No. 63/253,790 filed on Oct. 8, 2021, U.S. Provisional Application No. 63/280,953 filed on Nov. 18, 2021, U.S. Provisional Application No. 63/286,353 filed on Dec. 6, 2021. This application also claims the benefit U.S. Provisional Application No. 63/341,928 filed on May 13, 2022, and U.S. Provisional Application No. 63/343,963 filed on May 19, 2022. The text of each of the above-referenced (eleven) related applications is incorporated herein by reference in its entirety.

FIELD

The subject matter described herein relates to methods, systems, and apparatus for infusion of an antibody treatment to a patient, particularly for use in the treatment of a disease or condition.

SUMMARY

U.S. patent application Ser. No. 17/558,295, filed Dec. 21, 2021, describes methods, systems, and apparatus for administering an antibody treatment via an infusion device, e.g., a rapid infusion device, e.g., for the treatment of a disease or condition that requires one or more infusions of antibodies.

Described therein is a disposable infusion set for connection with the infusion device to facilitate delivery of a volume of solution comprising one or more antibodies to the patient, e.g., wherein the disposable infusion set comprises a needle (e.g., straight steel needle), one or more lengths of tubing, and/or an adhesive support (e.g., to avoid dislodging of the needle). Also described therein is a filter for filtering out particles (e.g., monoclonal antibody aggregates and/or polyclonal antibody aggregates) from the volume of solution prior to (upstream of) delivery of the filtered solution to the patient. As described therein, in some embodiments, the filter has a size small enough (e.g., a mesh tight enough) to catch the particles (e.g., monoclonal antibody aggregates and/or polyclonal antibody aggregates) (e.g., wherein the filter has a size below 170 microns, e.g., below 150 microns, e.g., below 125 microns, e.g., below 100 microns, e.g., below 75 microns, e.g., below 50 microns, e.g., below 40 microns, e.g., below 30 microns, e.g., below 20 microns, e.g., below 10 microns, e.g., below 8 microns, e.g., below 5 microns, e.g., below 4 microns, e.g., below 2 microns, e.g., below 1 micron, e.g., below 0.7 micron, e.g., below 0.5 micron, e.g., below 0.3 micron, e.g., about 0.2 µm).

Presented herein are methods, systems, and apparatus for administering an antibody treatment via an infusion device, e.g., a rapid infusion device, e.g., for the treatment of a disease or condition that requires one or more infusions of monoclonal and/or polyclonal antibodies.

In one aspect, the invention is directed to a disposable infusion set for use with an infusion device (e.g., a rapid infusion device) for administering by intravenous infusion a volume of solution comprising one or more antibodies [e.g., (i) one or more monoclonal and/or polyclonal antibodies (mAbs and/or pAbs) and/or (ii) one or more antibody drug conjugates (ADCs) and/or (iii) one or more lipid drug conjugates (LDCs) and/or (iv) intravenous immunoglobulin (IVIg)] to a patient, the disposable infusion set comprising a tubing line or lines and a filter (e.g., an inline filter), wherein the filter comprises a filter membrane that provides very low protein binding (e.g., negligible binding of the one or more antibodies to the filter membrane).

In certain embodiments, the filter membrane comprises polyethersulfone (PES).

In certain embodiments, the filter membrane comprises cellulose acetate.

In certain embodiments, the filter membrane has pore size less than 2 µm, or less than 1 µm, or less than 0.5 µm, or less than 0.3 µm (e.g., about 0.2 µm).

In certain embodiments, the disposable infusion set is configured (e.g., and approved) for use with a rapid infusion device (e.g., an infusion device capable of an infusion rate of at least 2 mL/min, e.g., at least 10 mL/min, e.g., at least 20 mL/min, e.g., at least 30 mL/min, e.g., at least 50 mL/min, e.g., at least 75 mL/min, e.g., at least 100 mL/min, e.g., at least 150 mL/min, e.g., at least 200 mL/min, e.g., at least 250 mL/min, e.g., at least 300 mL/min, e.g., at least 400 mL/min, e.g., at least 500 mL/min; e.g., an infusion device capable of infusion rates from about 2 mL/min to about 1500 mL/min).

In certain embodiments, the disposable infusion set does not include a coarse (e.g., with pore size greater than 100 µm or greater than 200 µm, e.g., 250 µm) filter (e.g., a blood filter, e.g., a filter that does not provide very low protein binding, e.g., a filter that is not made of PES or cellulose acetate).

In certain embodiments, the tubing line or lines fluidly connect (i) an intravenous (IV) bag or other receptacle containing the volume of solution to a pump capable of administering the volume of solution to the patient at a flow rate faster (e.g., substantially faster) than by gravity alone (e.g., faster than a gravity drip device) and/or (ii) the pump to the patient.

In certain embodiments, the filter provides for retention of bacteria and/or fungi, and/or wherein the filter provides for elimination of air from the solution passing therethrough.

In another aspect, the invention is directed to an infusion device (e.g., a rapid infusion device) for administering by intravenous infusion a volume of solution comprising one or more antibodies [e.g., (i) one or more monoclonal and/or polyclonal antibodies (mAbs and/or pAbs) and/or (ii) one or more antibody drug conjugates (ADCs) and/or (iii) one or more lipid drug conjugates (LDCs) and/or (iv) intravenous immunoglobulin (IVIg)] to a patient, the rapid infusion device comprising: a pump (e.g., a roller pump or centrifugal pump); and a disposable infusion set (e.g., the disposable infusion set of any one of claims 1 to 8) comprising a tubing line or lines and a filter (e.g., an inline filter), wherein the filter comprises a filter membrane that provides very low protein binding (e.g., negligible binding of the one or more antibodies to the filter membrane), wherein the tubing line or lines fluidly connect (i) an intravenous (IV) bag or other receptacle containing the volume of solution to the pump and/or (ii) the pump to the patient, and wherein the pump is configured such that one, two, or all three of (a), (b), and (c), as follows, applies: (a) the pump is capable of administering the volume of solution to the patient at a flow rate faster (e.g., substantially faster) than by gravity alone (e.g., faster than a gravity drip device); (b) the pump is capable of administering the volume of solution at a dosing rate of at least 35 mg of the one or more antibodies per minute and/or at a total antibody concentration of less than or equal to 20 mg/mL, [e.g., total mg of the one or more antibodies per mL IV solution]; and (c) the pump is capable of administering the volume of the solution in no more than 30 minutes.

In another aspect, the invention is directed to a method for administering an antibody treatment via an infusion device (e.g., a rapid infusion device), the method comprising: administering by intravenous infusion a volume of solution comprising one or more antibodies [e.g., (i) one or more monoclonal and/or polyclonal antibodies (mAbs and/or pAbs) and/or (ii) one or more antibody drug conjugates (ADCs) and/or (iii) one or more lipid drug conjugates (LDCs) and/or (iv) intravenous immunoglobulin (IVIg)] to a patient using an infusion device (e.g., a rapid infusion device), wherein the infusion device comprises a pump (e.g., a roller pump or centrifugal pump) and a disposable infusion set (e.g., the disposable infusion set of any one of the embodiments described herein) comprising a tubing line or lines and a filter (e.g., an inline filter), wherein the filter comprises a filter membrane that provides very low protein binding (e.g., negligible binding of the one or more antibodies to the filter membrane), wherein the tubing line or lines fluidly connect (i) an intravenous (IV) bag or other receptacle containing the volume of solution to the pump and/or (ii) the pump to the patient, for intravenous delivery of the volume of solution to the patient, wherein one, two, or all three of (a), (b), and (c), as follows, applies: (a) the pump administers the volume of solution to the patient at a flow rate faster (e.g., substantially faster) than by gravity alone (e.g., faster than a gravity drip device); (b) the pump administers the volume of solution at a dosing rate of at least 35 mg of the one or more antibodies per minute and/or at a total antibody concentration of less than or equal to 20 mg/mL [total mg of the one or more antibodies per mL IV solution]; and administration of the volume of solution to the patient is completed in no more than 30 minutes.

BRIEF DESCRIPTION OF THE DRAWINGS

Drawings are presented herein for illustration purposes, not for limitation. The foregoing and other objects, aspects, features, and advantages of the disclosure will become more apparent and may be better understood by referring to the following description taken in conjunction with the accompanying drawings, in which.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication is not an admission that the publication serves as prior art with respect to any of the claims presented herein. The Background section may include concepts informed by the embodiments recited in the claims and further described elsewhere in the specification. The discussion of concepts in the Background section is not an admission that the subject matter discussed is prior art.

Documents are incorporated herein by reference as noted. Where there is any discrepancy in the meaning of a particular term, the meaning provided in this document is controlling.

Headers are provided for the convenience of the reader—the presence and/or placement of a header is not intended to limit the scope of the subject matter described herein.

Figure 1:
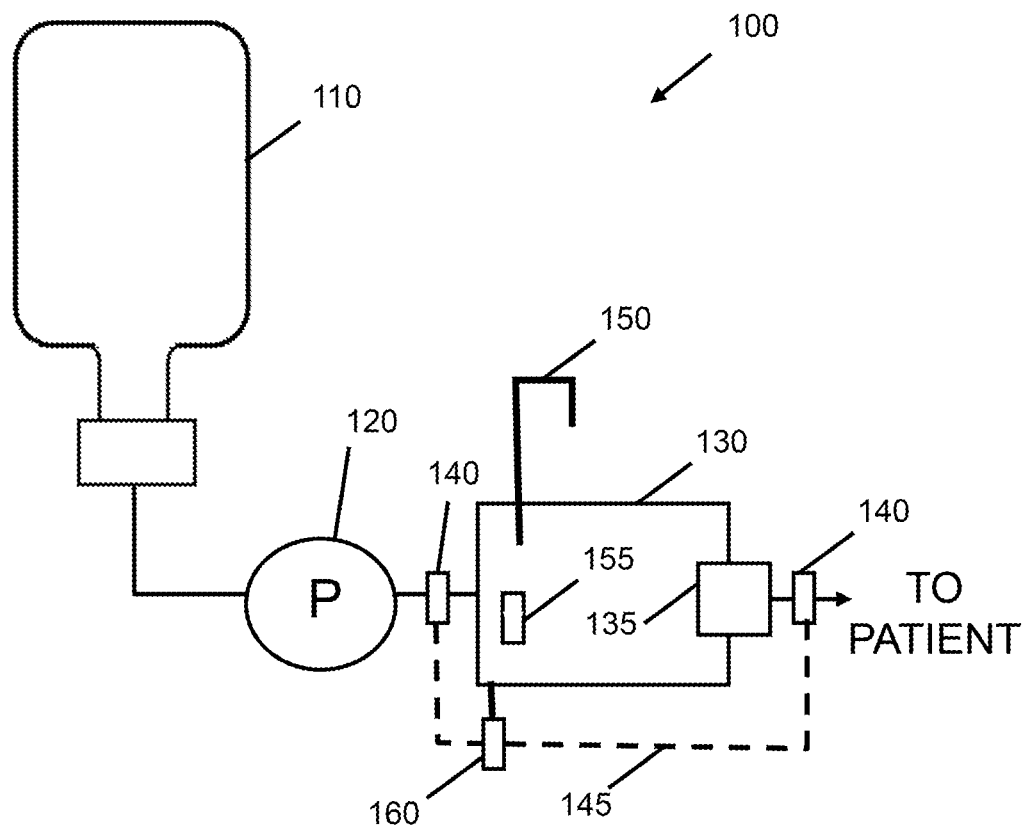
FIG. 1 shows a system and device for administering a monoclonal and/or polyclonal antibody solution via rapid infusion, according to an illustrative embodiment.

FIG. 1 shows an example of a rapid infusion system 100, in accordance with an illustrative embodiment of the invention. The rapid infusion system 100 includes an intravenous (IV) bag or other receptacle 110 containing a volume of drug solution to be administered to the patient. Elements of the rapid infusion system 100 are connected by tubing lines (e.g., a disposable set designed for one-time use). The drug solution is drawn from the IV bag or other receptacle 110 with pump 120 (e.g., a roller pump or centrifugal pump). Element 130 is a heater (which in some embodiments, may be optional) or other temperature control device. LY-CoV555 appears to be stable at room temperature for up to 7 hours; thus no special temperature controls may be needed during infusion. Additionally or alternatively, element 130 may optionally include one or more of a rate control device (e.g., a pressure-regulating valve 135, a pressure responsive valve 135, or the like), one or more sensors 140, and/or feedback circuitry 145. Heating element 130 may alternatively or additionally include an air venting mechanism 150.

In certain embodiments, element 130 includes (or is) a filter 155 for filtering out particles (e.g., monoclonal antibody aggregates and/or polyclonal antibody aggregates) from the volume of solution prior to (upstream of) delivery of the filtered solution to the patient. In certain embodiments, the filter 155 has a size small enough (e.g., a mesh tight enough) to catch the particles (e.g., monoclonal antibody aggregates and/or polyclonal antibody aggregates).

In certain embodiments, the filter 155 has a size below 170 microns (e.g., below 150 microns, e.g., below 125 microns, e.g., below 100 microns, e.g., below 75 microns, e.g., below 50 microns, e.g., below 40 microns, e.g., below 30 microns, e.g., below 20 microns, e.g., below 10 microns, e.g., below 8 microns, e.g., below 5 microns, e.g., below 4 microns, e.g., below 2 microns, e.g., below 1 micron, e.g., below 0.7 micron, e.g., below 0.5 micron, e.g., below 0.3 micron, e.g., about 0.2 µm). A standard filter size for blood administration is generally 170-260 microns, which is designed to trap fragments of cells, clots, or particulate matter that may develop as a result of blood product storage. However, particulate matter from antibody solutions is smaller (e.g., and/or the solution viscosity is less than that of blood), so a filter that traps smaller particles may be advantageously used for certain embodiments described herein.

The rapid infusion system 100 may include (e.g., as part or all of element 130, or as a separate element) an alarm 160 that identifies air or any other blockage in the line. The rapid infusion system 100 may include (e.g., as part or all of element 130, or as a separate element) an alarm 160 that identifies when a flow rate is above or below a prescribed rate. In certain alternative embodiments, element 130 is positioned between element 110 (IV bag or other receptacle) and the pump 120. In certain embodiments, element 130 (i.e., the heating element) is positioned downstream of pump 120.

Element 130 may have one or more components, any one or more of which may be in a different position with respect to other elements of the system than pictured in FIG. 1 (e.g., one or more elements of 130, e.g., a filter, may be positioned between IV bag 110 and pump 120, ahead of the pump, or may be part of the intravenous (IV) bag or other receptacle 110).

Figure 2:
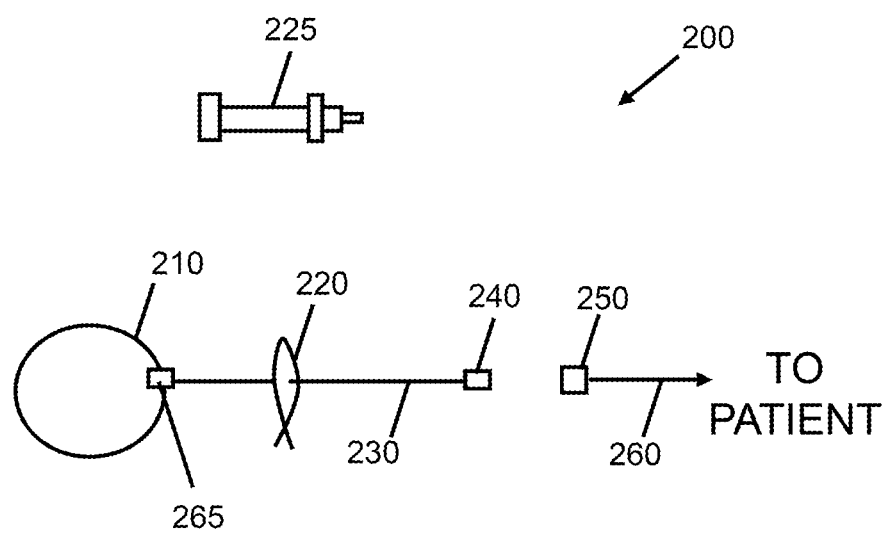
FIG. 2 shows another system and device for administering a monoclonal and/or polyclonal antibody solution via rapid infusion, according to an illustrative embodiment.

FIG. 2 shows an example of a rapid infusion system 200, in accordance with an illustrative embodiment of the present disclosure. The rapid infusion system 200 shown in FIG. 2 includes an elastomeric medicine ball 210 (also known as a "homeball," "ball pump," and/or "grenade pump"). The elastomeric medicine ball 210 may be used for drug delivery in place of the reservoir 110, pump 120, heating element 130, and/or other components illustrated in FIG. 1 and described above. In some embodiments, the system 200 may be used for administering rapid infusion to patients in their own homes, for example. Elastomeric medicine balls 210 are considered pumps, but they do not typically operate with electricity. Elastomeric pumps use pressure created by an elastomeric layer molded into the inside of the medicine ball 210 to infuse its fluid contents into a patient. In certain embodiments, the system 200 includes a pump line 230 that is configured to connect to a patient IV line 260 (that may be already installed (i.e., pre-installed) in the patient, or alternatively may be installed at the time of treatment). Prior to connection with the pump line 230, the patient IV line 260 may be flushed with saline solution (for example, via syringe 225) to ensure no clogs in the system 200, and then subsequently sanitized with alcohol wipes, especially at device access port (or hub) 250 (where contaminants could potentially enter the patient IV line 260). A pump line cap 240 can then be removed and the pump line 230 can be fluidly connected (for example, by inserting and twisting) into hub 250. When the patient is ready for drug delivery, clamp 220 can be removed from the pump line 230, and the drug will begin flowing into the patient via the patient IV line 260.

The elastomeric medicine ball 210, according to certain embodiments of the present disclosure, may be pre-filled with drug product (i.e., drug solution) and may be pre-pressurized. Once the clamp 220 is removed, the pressure within the elastomeric medicine ball 210 gradually forces the drug solution out of the elastomeric medicine ball 210, through the pump line 230 and patient IV line 260, and into the patient. In certain embodiments, the delivery process for a single administration can take as long as 90 minutes, but is preferably a shorter time period, for example, administration is completed in no more than 30 minutes (e.g., no more than 25 minutes, e.g., no more than 20 minutes, e.g., no more than 15 minutes, e.g., no more than 10 minutes, e.g., no more than 5 minutes). Elastomer balls generally have a flow restrictor 265 to control the accuracy of the rate of flow. The flow restrictor 265 may be, for example, a steel cannula or a glass capillary molded into system tubing or located inside the elastomeric reservoir. Standard elastomer balls generally provide a flow rate of up to about 250 mL/hr (about 4.17 mL/min). For the methods described herein, elastomer balls may be engineered to permit higher flow rate, for example, flow rate substantially faster than IV flow by gravity alone (e.g., the elastomer ball system provides a flow rate of at least 10 mL/min, or at least 15 mL/min, or at least 20 mL/min, or at least 25 mL/min, or at least 30 mL/min, or at least 35 mL/min, or at least 40 mL/min, or at least 45 mL/min, or at least 50 mL/min). Total drug delivery volumes per elastomeric medicine ball 210 may range up to about 500 mL (e.g., the total volume may be about 50 mL, about 100 mL, about 150 mL, about 250 mL, about 350 mL, about 450 mL, about 500 mL, or within ±50 mL ranges of each of these figures).

In some embodiments, where higher diffusion rates are required, a patient IV line 260 can be installed in each arm (or, alternatively, in one or more other locations of the body), each patient IV line 260 connecting to a separate elastomeric medicine ball 210. In certain embodiments, because the elastomeric medicine ball 210 is calibrated according to the inherent back pressure or resistance in the pump line 230, patient IV line 260, and patient himself/herself, the elastomeric medicine ball 210 generally would not be used in connection with, for example, the fluid heater 130 (shown in FIG. 1). Accordingly, where the contents must be kept refrigerated before use, each elastomeric medicine ball 210 should be removed from the refrigerator with enough time to warm up to room temperature (for example, 10-30 minutes, or about 10-20 minutes) prior to use. However, care should be taken not to expose each elastomeric medicine ball 210 to room temperature for a prolonged period of time, to avoid spoiling and/or breakdown of the drug product.

Still referring to FIG. 2, the system 200 may include one or more elastomeric medicine balls 210 that use only the pressure within each elastomeric medicine ball 210, and not gravity or a separate pump, for drug delivery. As such, patients have the ability to move around and carry the one or more elastomeric medicine balls 210 with them (for example, in a pocket or pockets, etc.) as the drug is flowing. In certain embodiments, once the treatment is complete, each elastomeric medicine ball 210 will be fully deflated, and the pump line 230 can be removed from the device access port 250 (or hub 250). The elastomeric medicine ball 210, pump line 230, clamp 220, and cap 240 can then be disposed of. In certain embodiments, post treatment flushing of the patient IV line 260 should be performed to ensure any drug solution still in the patient IV line at the end of treatment in pushed through the patient IV line 260 into the patient. In certain embodiments, final (i.e., post flushing) sterilization of the hub or device access port 250 should be performed, and the device access port should be capped after sterilization. In some embodiments, heparin may be administered before and/or after the final flushing to avoid clotting, depending on the patient needs. In some embodiments, the system 200 shown in FIG. 2 may also include a heating element in fluid communication with the drug IV line 230 (i.e., downstream of the ball pump 210) to more rapidly heat the infusate. The system 200 may also include an additional pump fluidly upstream of the heating element in order to overcome any addition flow restriction or pressure drop introduced by the heating element.

Figure 3:
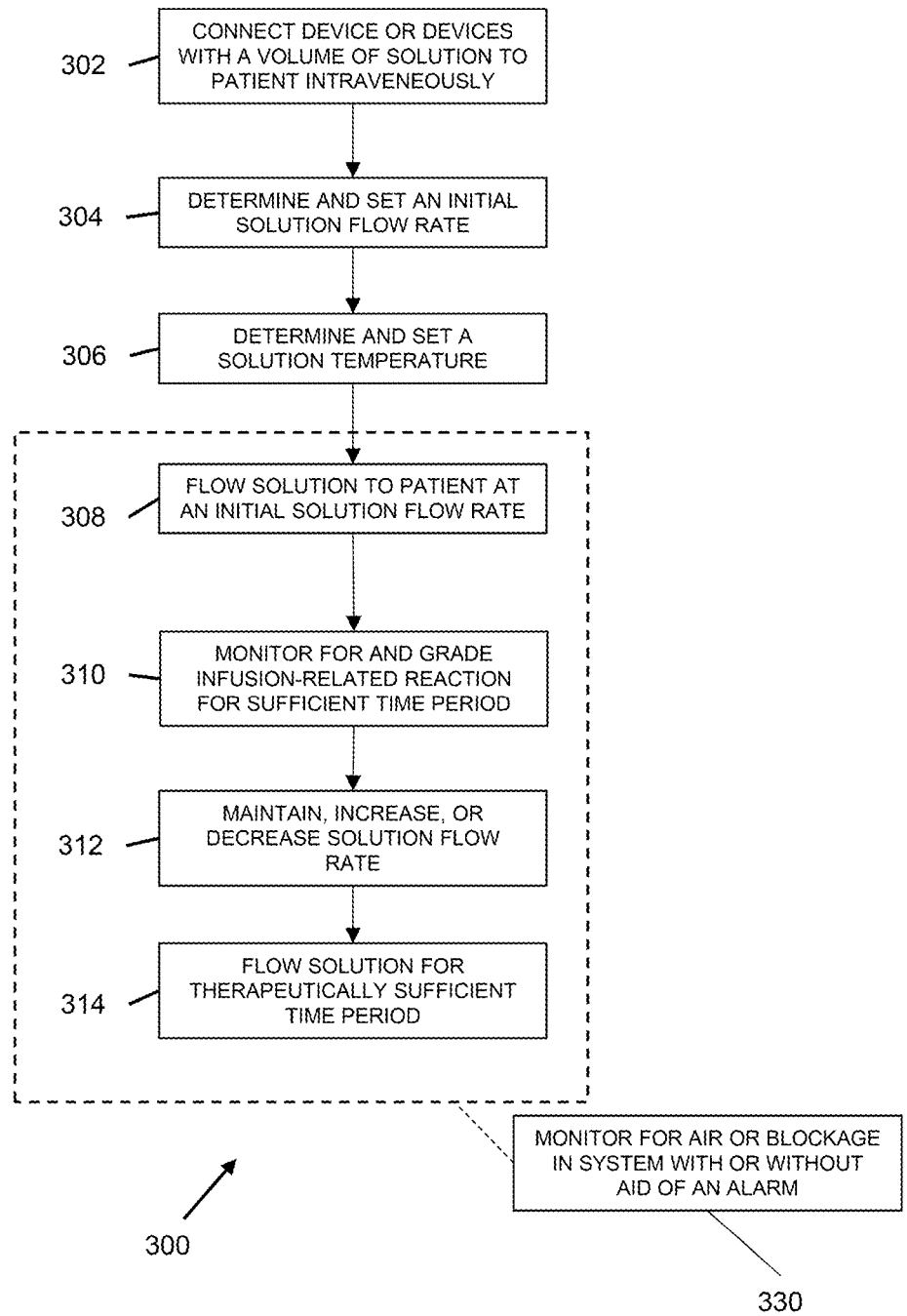
FIG. 3 shows a method of using devices for administering a monoclonal and/or polyclonal antibody solution via rapid infusion, according to an illustrative embodiment.

FIG. 3 illustrates a method 300 for systems 100 and/or 200, according to aspects of the present embodiments. Prior to step 302, the method 300 for system 200 may include using a syringe 225 and flushing the intravenously-attached system at port 250 with saline.

Still referring to FIG. 3, in step 304, a solution flow rate may be determined according to various embodiments of system 100 and may be controlled using a flow-controlling device 120. At step 304, an initial solution flow rate may be determined according to various embodiments of system 200 and may be controlled using a flow-controlling device 210. The initial solution flow rate may be 50 mg/hr, 100 mg/hr, or from about 25 mg/hr to about 75 mg/hr, or in other embodiments from about 75 mg/hr to about 125 mg/hr. The flow rate may then be increased in increments of about 25 mg/hr, 50 mg/hr, and/or 100 mg/hr, at time intervals of about 1 minute, 2 minutes, 5 minutes, 10 minutes, 15 minutes, 20, minutes, and/or 30 minutes, to a maximum flow rate of about 400 mg/hr, or from about 300 mg/hr to about 450 mg/hr, or from about 250 mg/hr to about 500 mg/hr, or from about 150 mg/hr to about 450 mg/hr.

Still referring to FIG. 3, in step 306, a solution temperature may be determined according to various embodiments of system 100 and a solution temperature may be set using an optional temperature-controlling device 130. In step 306, a solution temperature may be determined according to various embodiments of system 200 and a solution temperature may be set by equilibrating a solution to an ambient temperature or physiologically-relevant temperature.

Still referring to FIG. 3, in step 308, rapid infusion is started by flowing a solution at an initial flow rate determined by various embodiments of the invention. In step 310, the patient is monitored and graded for infusion-related reactions (IRR).

Still referring to FIG. 3, in step 312, a solution flow rate is maintained, increased, or decreased based on IRR grading and according to various embodiments of the present invention. In step 312, solution flow rate may be maintained for a patient presenting no IRR or presenting a minor IRR after an initial solution flow and being treated using an embodiment of system 100 or an embodiment of system 200. In step 312, solution flow rate may be increased for a patient presenting no IRR or presenting a minor IRR after an initial solution flow and being treated using an embodiment of system 100 or an embodiment of system 200. In step 312, solution flow rate may be increased for a patient presenting no IRR or presenting a minor IRR after an initial solution flow and being treated using an embodiment of system 100 or an embodiment of system 200.

Still referring to FIG. 3, in step 314 a solution may be continued to flow at a flow rate previously determined in method 300 for a time period sufficient for providing disease therapy. At step 330, the method 300 may include monitoring for air and/or blockage in the system (for example, with or without the air of alarm 160) during the entire period of time that solution is flowing (i.e., steps 308-314 in FIG. 3). In some embodiments, prior to step 302, a volume of therapeutic solution may be loaded into any device or devices (for example, 110, 210, 225) as needed according to aspects of the present disclosure.

Figure 4:
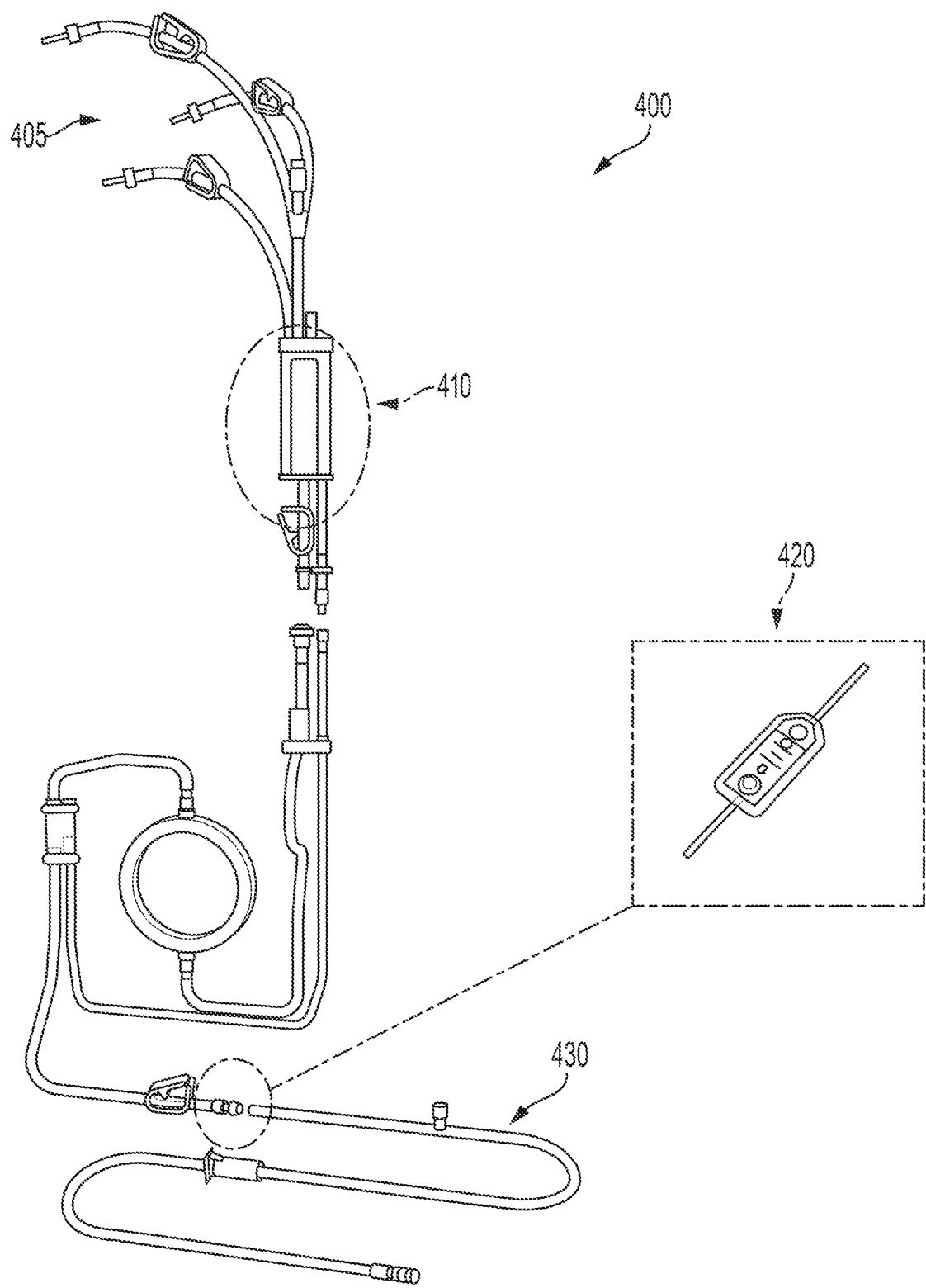
FIG. 4 depicts an illustrative disposable infusion set manufactured by Belmont Medical Technologies (3-Spike Disposable Set) (400), originally designed for rapid delivery of warmed blood, with noted design modifications to make the disposable set compatible for use with an infusion device (e.g., a rapid infusion device) for infusion of an antibody treatment to a patient, according to illustrative embodiments of the present disclosure.

FIG. 4 depicts an illustrative disposable infusion set manufactured by Belmont Medical Technologies (3-Spike Disposable Set) (400), originally designed for rapid delivery of warmed blood, with noted design modifications to make the disposable set compatible for use with an infusion device (e.g., a rapid infusion device) for infusion of an antibody treatment to a patient. In short, the existing reservoir chamber and coarse filter (410) is removed in the modified design, and an inline filter (420), for example, a 0.2 µm polyethersulfone (PES) inline filter, is added. The inline filter (420) may be positioned, for example, at the connection to a patient line extension (430), as pictured, though other positions may be chosen, and a patient line extension may not be needed. In certain embodiments, the added inline filter (420) also provides air venting. Furthermore, the circular heat exchanger portion shown in FIG. 4, with high surface area stainless steel rings, may be removed, e.g., where no heating of the delivered solution is required. A pressure chamber and air detector is pictured to the left of the circular heat exchanger portion in FIG. 4, with the fluid path splitting into an infuse line extending from the air detector to the patient line extension (430), and a recirculate line extending below the heat exchanger portion and back up. The modified design (for delivery of an antibody treatment) need not include a recirculate line, and, in certain embodiments, the pressure chamber and/or air detector is/are not needed or is/are positioned elsewhere in the disposable set. The disposable set pictured in FIG. 4 has connections between a heat exchanger, reservoir, and patient line. Where a heat exchanger and/or reservoir is/are not needed, further modifications of this arrangement can be made to adapt the set for use with infusion of treatment solutions.

It is presently found that non-PES coarse blood filters (e.g., 250 µm) such as used with the 120 mL reservoir chamber 410 for infusion of blood or plasma (the original purpose of rapid infusion devices) may clog if used to filter antibody infusions, e.g., solutions of monoclonal and/or polyclonal antibodies (mAbs and/or pAbs), antibody drug conjugates (ADCs), lipid drug conjugates (LDCs), and/or intravenous immunoglobulin (IVIg). An example of a PES filter suitable to filter antibody infusions, which can be integrated as an inline filter 420 in the disposable filter set 400 of FIG. 4, is the Sterifix® 0.2 µm infusion filter manufactured by B. Braun. The inline filter 420 provides retention of undesired particles, bacteria, and fungi, and provides for elimination of air, while avoiding binding of antibodies. The filter has a Supor® membrane made of PES with effective filtration area of 10 $cm^2$. Other non-PES filters can potentially bind antibodies, e.g., monoclonal antibodies (mAbs), from the treatment solution such that it is retained in the filter rather than being delivered to the patient. PES has been found to provide low protein-binding, with negligible binding of mAbs to the filter membrane. Another filter membrane material that provides very low protein binding is cellulose acetate, and hence, in certain embodiments, may be used for mAbs delivery via infusion (e.g., rapid infusion). Regenerated cellulose has low protein binding but higher than PES and cellulose acetate. Nylon has low to moderate protein binding, and cellulose nitrate has high protein binding.

In certain embodiments, the infusion device (e.g., rapid infusion device) includes a disposable set with a sterile fluid path intended for single-use, with standard luer connectors for connection to a standard catheter and a pressure-regulating valve (PRV) at the input to protect the disposable set and the patient from unintended exposure to high pressure applied to the intravenous (IV) line, wherein the PRV may allow an increase of flow from a low level to a higher level by application of a pressure (e.g., up to 300 mmHg), but will prevent pressure higher than this from reaching the set or IV line distal to it. In certain embodiments, the infusion device also includes a check valve at the output to prevent back flow. In certain embodiments, drug administration is simplified by provision of a portable infusion system (e.g., a portable rapid infusion system) with disposable tubing lines already attached, e.g., where the entire infusion system, pump included, is designed for a single use. Further simplification may be possible by providing the IV bag (or other receptacle) pre-loaded with drug solution (e.g., pre-made drug solution) in the appropriate amount and at the appropriate concentration (e.g., all in a self-contained kit). Providing a pre-made solution may not be possible for certain drugs.

In one aspect, the invention is directed to a disposable infusion set for use with an infusion device (e.g., a rapid infusion device) for administering by intravenous infusion a volume of solution comprising one or more antibodies [e.g., (i) one or more monoclonal and/or polyclonal antibodies (mAbs and/or pAbs) and/or (ii) one or more antibody drug conjugates (ADCs) and/or (iii) one or more lipid drug conjugates (LDCs) and/or (iv) intravenous immunoglobulin (IVIg)] to a patient, the disposable infusion set comprising a tubing line or lines and a filter (e.g., an inline filter), wherein the filter comprises a filter membrane that provides very low protein binding (e.g., negligible binding of the one or more antibodies to the filter membrane).

In certain embodiments, the filter membrane comprises polyethersulfone (PES).

In certain embodiments, the filter membrane comprises cellulose acetate.

In certain embodiments, the filter membrane has pore size less than 2 µm, or less than 1 µm, or less than 0.5 µm, or less than 0.3 µm, or about 0.2 µm.

In certain embodiments, the disposable infusion set is configured (e.g., and approved) for use with a rapid infusion device (e.g., an infusion device capable of an infusion rate of at least 2 mL/min, e.g., at least 10 mL/min, e.g., at least 20 mL/min, e.g., at least 30 mL/min, e.g., at least 50 mL/min, e.g., at least 75 mL/min, e.g., at least 100 mL/min, e.g., at least 150 mL/min, e.g., at least 200 mL/min, e.g., at least 250 mL/min, e.g., at least 300 mL/min, e.g., at least 400 mL/min, e.g., at least 500 mL/min; e.g., an infusion device capable of infusion rates from about 2 mL/min to about 1500 mL/min).

In certain embodiments, the disposable infusion set does not include a coarse (e.g., with pore size greater than 100 µm or greater than 200 µm, e.g., 250 µm) filter (e.g., a blood filter, e.g., a filter that does not provide very low protein binding, e.g., a filter that is not made of PES or cellulose acetate).

In certain embodiments, the tubing line or lines fluidly connect (i) an intravenous (IV) bag or other receptacle containing the volume of solution to a pump capable of administering the volume of solution to the patient at a flow rate faster (e.g., substantially faster) than by gravity alone (e.g., faster than a gravity drip device) and/or (ii) the pump to the patient.

In certain embodiments, the tubing line or lines (and/or pump surfaces that come into contact with the pumped fluid) is/are constructed of a medical-grade plastic such as polyvinyl chloride (PVC), polyethylene, a thermoplastic elastomer (TPE), nylon, and/or silicone.

In certain embodiments, the filter provides for retention of bacteria and/or fungi, and/or wherein the filter provides for elimination of air from the solution passing therethrough.

In another aspect, the invention is directed to an infusion device (e.g., a rapid infusion device) for administering by intravenous infusion a volume of solution comprising one or more antibodies [e.g., (i) one or more monoclonal and/or polyclonal antibodies (mAbs and/or pAbs) and/or (ii) one or more antibody drug conjugates (ADCs) and/or (iii) one or more lipid drug conjugates (LDCs) and/or (iv) intravenous immunoglobulin (IVIg)] to a patient, the rapid infusion device comprising: a pump (e.g., a roller pump or centrifugal pump); and a disposable infusion set (e.g., any of the disposable infusion sets described herein) comprising a tubing line or lines and a filter (e.g., an inline filter), wherein the filter comprises a filter membrane that provides very low protein binding (e.g., negligible binding of the one or more antibodies to the filter membrane), wherein the tubing line or lines fluidly connect (i) an intravenous (IV) bag or other receptacle containing the volume of solution to the pump and/or (ii) the pump to the patient, and wherein the pump is configured such that one, two, or all three of (a), (b), and (c), as follows, applies: (a) the pump is capable of administering the volume of solution to the patient at a flow rate faster (e.g., substantially faster) than by gravity alone (e.g., faster than a gravity drip device); (b) the pump is capable of administering the volume of solution at a dosing rate of at least 35 mg of the antibodies per minute and/or at a total antibody concentration of less than or equal to 20 mg/mL, [total mg of the one or more antibodies per mL IV solution]; and (c) the pump is capable of administering the volume of the solution in no more than 30 minutes.

In another aspect, the invention is directed to a method for administering an antibody treatment via an infusion device (e.g., a rapid infusion device), the method comprising: administering by intravenous infusion a volume of solution comprising one or more antibodies [e.g., (i) one or more monoclonal and/or polyclonal antibodies (mAbs and/or pAbs) and/or (ii) one or more antibody drug conjugates (ADCs) and/or (iii) one or more lipid drug conjugates (LDCs) and/or (iv) intravenous immunoglobulin (IVIg)] to a patient using an infusion device (e.g., a rapid infusion device), wherein the infusion device comprises a pump (e.g., a roller pump or centrifugal pump) and a disposable infusion set (e.g., the disposable infusion set of any of the embodiments described herein) comprising a tubing line or lines and a filter (e.g., an inline filter), wherein the filter comprises a filter membrane that provides very low protein binding (e.g., negligible binding of the one or more antibodies to the filter membrane), wherein the tubing line or lines fluidly connect (i) an intravenous (IV) bag or other receptacle containing the volume of solution to the pump and/or (ii) the pump to the patient, for intravenous delivery of the volume of solution to the patient, wherein one, two, or all three of (a), (b), and (c), as follows, applies: (a) the pump administers the volume of solution to the patient at a flow rate faster (e.g., substantially faster) than by gravity alone (e.g., faster than a gravity drip device); (b) the pump administers the volume of solution at a dosing rate of at least 35 mg of the one or more antibodies per minute and/or at a total antibody concentration of less than or equal to 20 mg/mL [total mg of the one or more antibodies per mL IV solution]; and (c) administration of the volume of solution to the patient is completed in no more than 30 minutes.

In some embodiments, the one or more monoclonal and/or polyclonal antibodies comprises a monoclonal and/or polyclonal antibody (or cocktail of antibodies) for the treatment of one or more members selected from the group consisting of cancer (e.g., colorectal, lung, glioblastoma, kidney, breast, stomach, esophageal, cervical, or ovarian cancer, or multiple myeloma, soft tissue sarcoma, lymphoma, melanoma, neuroblastoma, or leukemia), a neurological disease or condition {e.g., Alzheimer's disease (AD), Parkinson's disease (PD); Duchene's muscular dystrophy (DMD); multiple sclerosis (MS); myasthenia gravis; migraine; migraine and cluster headache; neuromyelitis optica spectrum disorder (NMOSD); idiopathic inflammatory myopathies (IIM); immune-related peripheral neuropathies (multifocal motor neuropathy (MMN), anti-myelin associate glycoprotein (anti-MAG) neuropathy, chronic inflammatory demyelinating polyneuropathy (CIDP)); or a neurooncological condition (e.g., malignant glioma or recurrent glioblastoma)}; dermatitis; psoriasis; asthma or other respiratory disease; macular degeneration; an autoimmune disease (e.g., rheumatoid arthritis, Crohn's disease, lupus, or ulcerative colitis); cytokine release syndrome; Castelman disease; a disease caused by a pathogen (e.g., infection or other disease caused by a virus, bacteria, fungus, or protozoa); and organ and/or tissue transplant.

In some embodiments, the one or more monoclonal and/or polyclonal antibodies comprises a member selected from the group consisting of the following: an anti-inflammatory (e.g., infliximab, adalimumab, basiliximab, daclizumab, or omalizumab); an anti-cancer (e.g., gemtuzumab, alemtuzumab, rituximab, trastuzumab, nimotuzumab, cetuximab, or bevacizumab & ranibizumab); an anti-cancer and anti-viral (e.g., bavituximab); palivizumab; and abciximab.

In some embodiments, the method is performed for the treatment of COVID-19 (i.e., caused by the virus SARS-CoV-2) [e.g., wherein the one or more monoclonal and/or polyclonal antibodies comprises one or more members selected from the group consisting of bamlanivimab (aka LY-CoV555, Eli Lilly); bamlanivimab and etesevimab antibody cocktail (aka LY-CoV555 (bamlanivimab)+JS016 (etesevimab) antibody cocktail, Eli Lilly); casirivimab and imdevimab antibody cocktail (aka REGN-COV2 aka REGEN-COV™ aka REGN10933+REGN10987, aka Ronapreve, Regeneron, Roche); gimsilumab (Roivant Sciences); tocilizumab (aka Actemra, Genentech); B38, H4, B5 and/or H2 Capital Medical University, Beijing; COVI-GUARD™ (STI-1499) and/or COVI-AMG™ (STI-2020) (Sorrento Therapeutics); regdanvimab aka Regkirona (Celltrion); sotrovimab (aka VIR-7831 aka Xevudy) and/or VIR-7832, Vir Biotechnology); and tixagevimab and cilgavimab antibody cocktail (aka Evusheld, AstraZeneca)].

In some embodiments, the method is performed for the treatment of a neurological disease or condition {e.g., Alzheimer's disease (AD), Parkinson's disease (PD); Duchene's muscular dystrophy (DMD); multiple sclerosis (MS); myasthenia gravis; migraine; migraine and cluster headache; neuromyelitis optica spectrum disorder (NMOSD); idiopathic inflammatory myopathies (IIM); immune-related peripheral neuropathies (multifocal motor neuropathy (MMN), anti-myelin associate glycoprotein (anti-MAG) neuropathy, chronic inflammatory demyelinating polyneuropathy (CIDP)); or a neurooncological condition (e.g., malignant glioma or recurrent glioblastoma)} [e.g., wherein the one or more monoclonal antibodies comprises one or more members selected from the group consisting of aducanumab (Biogen Inc.), gantenerumab (Chugai Pharmaceutical Co., Ltd., Hoffmann-La Roche), donanemab (Eli Lilly and Company), BAN2401 (Eisai Co., Ltd. and Biogen Inc.), gosuranemab (Biogen Inc., Bristol-Myers Squibb), zagotenemab (Eli Lilly and Company), tilavonemab (AbbVie, C2N Diagnostics, LLC), semorinemab (AC Immune SA, Genentech, Hoffmann-La Roche), cinpanemab (Biogen, Neurimmune), MEDI1341 (AstraZeneca, Takeda Pharmaceutical Company), domagrozumab (Pfizer Inc.), natalizumab (humanized Ab directed against α4 β1 integrin) (Biogen Inc.), alemtuzumab (Sanofi), ocrelizumab (Genentech USA, Inc.), ofatumumab (Novartis Pharmaceuticals Corporation), inebilizumab (Horizon Therapeutics plc), erenumab (Amgen Inc.), fremanezumab (Teva Pharmaceuticals USA, Inc.), eptinezumab (Lundbeck), galcanezumab (Lilly USA, LLC), rituximab (Amgen Inc.), eculizumab (Alexion Pharmaceuticals, Inc.), tocilizumab (Genentech, Inc.), satralizumab (Genentech USA, Inc.), ravulizumab (Alexion Pharmaceuticals, Inc.), aquaporumab, infliximab (Amgen Inc.), rozanolixizumab, nipocalimab (Johnson & Johnson Inc.), batoclimab (Harbour BioMed), efgartigimod (Argenx), bevacizumab (Pfizer Inc.), and rilotumumab (Amgen, Inc.).

In some embodiments, the one or more monoclonal antibodies comprises one or more members selected from the group consisting of: pembrolizumab (Keytruda), manufactured by Merck for treatment of cancer; nivolumab (Opdivo), manufactured by Bristol Myers Squibb, for various forms of cancer; bevacizumab (Avastin), manufactured by Roche, for colorectal, lung, glioblastoma, kidney, cervical, and/or ovarian cancer; ocrelizumab (Ocrevus), manufactured by Roche, for relapsing or primary progressive multiple sclerosis; rituximab (Rituxan), manufactured by Roche, Pharmstandard, for various autoimmune diseases and cancers; daratumumab (Darzalex), manufactured by Janssen (Johnson & Johnson), for multiple myeloma; pertuzumab (Perjeta), manufactured by Roche, for HER2-positive breast cancer; trastuzumab (Herceptin), manufactured by Genentech (Roche), for breast, stomach, and esophageal cancer; infliximab (Remicade), manufactured by Janssen (Johnson & Johnson), for Crohn's disease, ulcerative colitis, rheumatoid arthritis, ankylosing spondylitis, psoriatic arthritis, and plaque psoriasis; tocilizumab (Actemra/RoActemra), manufactured by Roche, for rheumatoid arthritis, forms of juvenile idiopathic arthritis and giant cell arteritis as well as CART cell-induced severe or life-threatening cytokine release syndrome; atezolizumab (Tecentriq), manufactured by Roche, for urothelial carcinoma, non-small cell lung cancer, and triple-negative breast cancer; tositumomab-I131 (Bexxar), manufactured by GSK, for non-Hodgkin lymphoma; olaratumab (Lartruvo), manufactured by Eli Lilly, for soft tissue sarcoma; MabThera, rituximab (Rituxan), manufactured by Biogen/Genentech, for non-Hodgkin lymphoma; basiliximab (Simulect), manufactured by Novartis, for prevention of kidney transplant rejection; ibritumomab tiuxetan (Zevalin), manufactured by Spectrum, for non-Hodgkin lymphoma; cetuximab (Erbitux), manufactured by Bristol Meyers Squibb, Eli Lilly, and Merck, for colorectal cancer; natalizumab (Tysabri), manufactured by Biogen/Elan, for multiple sclerosis; panitumumab (Vectibix), manufactured by Amgen, for colorectal cancer; ranibizumab (Lucentix), manufactured by Genentech/Novartis, for macular degeneration; eculizumab (Soliris), manufactured by Alexion, for paroxysmal nocturnal hemoglobinuria; ofatumumab (Arzerra), manufactured by Novartis, for chronic lymphocytic leukemia; belimumab (Benlysta), manufactured by Human Genome Sciences, for systemic lupus erythematosus; ipilimumab (Yervoy), manufactured by Bristol Meyers Squibb, for metastatic melanoma; pertuzumab (Perjeta), manufactured by Genentech, for breast cancer; raxibacumab, manufactured by Human Genome Sciences, for anthrax infection; obinutuzumab (Gazyva, Gazyvaro), manufactured by Genentech, for chronic lymphocytic leukemia; siltuximab (Sylvant), manufactured by Janssen Biotech), for Castelman disease; ramucirumab (Cyramza), manufactured by Eli Lilly, for gastric cancer; vedolizumab (Entyvio), manufactured by Takeda, for ulcerative colitis, Crohn's disease; alemtuzumab (Lemtrada, MabCampath, Campath-1H), manufactured by Genzyme, for multiple sclerosis and chronic myeloid leukemia, necitumumab (Portrazza), manufactured by Eli Lilly, for non-small cell lung cancer; dinutuximab (Qarziba, Unituxin), manufactured by United Therapeutics, for neuroblastoma; elotuzumab (Empliciti), manufactured by Bristol Meyers Squibb, for multiple myeloma; reslizumab (Cinqaero, Cinqair), manufactured by Teva, for asthma; bezlotoxumab (Zinplava), manufactured by Merck Sharp Dohme, for prevention of *Clostridium difficile* infection recurrence; obiltoxaximab (Anthim), for prevention of inhalational anthrax; avelumab (Bavencio), manufactured by Merck, for Merkel cell carcinoma; and durvalumab (Imfinzi), manufactured by AstraZeneca, for bladder cancer.

In some embodiments, the method is performed for the treatment of an organ and/or tissue transplant patient [e.g., wherein the one or more polyclonal and/or monoclonal antibodies comprises one or more members selected from the group consisting of anti-thymocyte globulin [rabbit] (Thymoglobulin, Sanofi), lymphocyte immune globulin, anti-thymocyte globulin [equine] sterile solution (Atgam, Pfizer), alemtuzumab (Sanofi), rituximab (Amgen Inc), alpha-1 antitrypsin, and a double antibody conjugate that is an anti-CD3 and anti-CD7 agent].

In certain embodiments, the volume of solution being rapidly infused to the patient comprises one or more antibody drug conjugates (ADCs) and/or lipid drug conjugates (LDCs) [lipoidal prodrug—bioactive molecules covalently or non-covalently linked with lipids like fatty acids, glycerides, or phospholipids]. Examples of ADCs include the following: ado-trastuzumab emtansine (Kadcyla™, manufactured by Genentech, Roche), brentuximab vedotin (Adcetris™, manufactured by Seattle Genetics, Millennium/Takeda), inotuzumab ozogamicin (Besponsa™, manufactured by Pfizer/Wyeth), gemtuzumab ozogamicin (Mylotarg™, manufactured by Pfizer/Wyeth), Moxetumomab pasudotox (Lumoxiti™, manufactured by Astrazeneca), polatuzumab vedotin-piiq (Polivy™, manufactured by Genentech, Roche), Enfortumab vedotin (Padcev™, manufactured by Astellas/Seattle Genetics), Sacituzumab govitecan (Trodelvy, manufactured by Immunomedics), Trastuzumab deruxtecan (Enhertu™, manufactured by AstraZeneca/Daiichi Sankyo), belantamab mafodotin-blmf (Blenrep™, manufactured by GlasoSmithKline), loncastuximab tesirine-Ipyl (ZYNLONTA™, manufactured by ADC Therapeutics), and tisotumab vedotin-tftv (Tivdak, manufactured by Seagen Inc.).

In certain embodiments, the volume of solution being rapidly infused to the patient comprises an immunoglobulin (IVIg) preparation. Example commercial IVIG preparations include the following: Gammagard S/D (Baxter/Hyland), Gammunex (Bayer), Intratect (Biotest Pharma), Kiovig (Baxter), Octagam (Octapharma), Pentaglobin (Biotest Pharma), and Sandoglobulin (CSL Behring).

In certain embodiments, the infusion device for which the disposable infusion set is designed to be used is a rapid infusion device, though in other embodiments, the infusion device is not a rapid infusion device.

Commercially available rapid infusion devices are currently designed to rapidly administer a large volume of plasma, blood, or other fluid to patients in military or civilian emergency situations, for example, a patient suffering from a traumatic injury such as uncontrolled hemorrhage. These systems typically feature a roller pump, centrifugal pump, or other pump mechanism, often with a warmer or other temperature control device. Examples of commercially available rapid infusion systems include the Hotline HL-1200A Rapid Infuser Infusion Pump (capable of infusion rates from 30 mL/min to 1100 mL/min, with maximum rate of 1400 mL/min) (Smiths Group Plc, London, UK); the Belmont® Rapid Infuser RI-2 (capable of infusion rates from 2.5 mL/min to 1000 mL/min), the FMS2000, the Buddy™ and the buddy Lite™ portable IV & infusion pump (Belmont Medical Technologies, Billerica, Mass.); LifeFlow Rapid Fluid Infuser, and LifeFlow Plus Rapid Fluid and Blood Infuser (capable of 500 mL of fluid in less than 2 min, 20G IV catheter, or 274 mL/min via 18ga catheter) (410 Medical, Durham, N.C.); Thermacor 1200 (capable of infusion rates from 10 mL/hour to 1200 mL/min) (Smisson-Cartledge Biomedical, Macon, GA); The Warrior lite, Warrior, Warrior EXTREME, Warrior Hybrid, and Warrior AC (QinFlow Ltd. of Rosh Ha'ayin Israel); enFlow® IV fluid and blood warming system (CareFusion, Vernon Hills, Ill.); Medi-Temp by Stryker (Kalamazoo, Mich.); Ranger by 3M (St. Paul, Minn.); Level 1 h-1200 Fast Flow Fluid Warmer (Smiths Medical, Dublin, Ohio); and Thermal Angel® blood and IV fluid infusion warmer (Estill Medical Technologies, Inc., Arlington, Tex.). Devices with proprietary tubing sets include the enFlow with a 4-mL priming volume and a flow rate up to 200 mL/minute; the Medi-Temp with a flow rate up to 500 mL/minute; and the Ranger by 3M (St. Paul, Minn.) with a flow rate up to 500 mL/minute. The portable Belmont® Buddy™ system is designed for flow rates up to 100 mL/min for crystalloids at 20° C. and up to 50 mL/min for packed red cells at 10° C. The portable, battery powered buddy Lite™ system is designed for maximum flow rates of 50-80 mL/min, depending on the input temperature. Pressurized devices for massive transfusion of blood include the Belmont Rapid Infuser RI-2 which can deliver a flow rate of more than 750 mL/minute (e.g., up to 1500 mL/minute); the Level 1 h-1200 Fast Flow Fluid Warmer which can infuse fluids at flows of up to 600 mL/min. Many of the above devices (including the portable devices) include a flow control system and/or other flow and/or metering control devices, such as pressure-regulating valves (PRVs) and/or pressure-responsive valves, to control the specific flow rate of a liquid delivered to the patient and/or to ensure the flow stays below a predetermined maximum flow rate and/or above a predetermined minimum flow rate. Moreover, these flow control devices and/or systems may allow the operator to establish an initial lower flow rate, then increase to a safe higher flow rate if no serious IRRs are observed in the patient.

These rapid infusion systems are not currently used for administration of drugs. Rapid infusion systems include those described in any of the following U.S. patents and published patent application, the disclosures of which are incorporated herein by reference: U.S. Pat. Nos. 5,319,170; 6,175,688; 6,236,809; 6,480,257; 7,819,875; 9,737,672;

10,293,099; and 10,485,936; and U.S. Patent Application Publication No. 2009/0192446 (U.S. patent application Ser. No. 12/228,618).

Unlike normal IV lines with gravity fed administration (drip IV), a rapid infusion device does not need a drip chamber to gauge flow rates, since a software-controlled pump is used to administer the fluids. By eliminating the drip chamber, a rapid infusion device provides for administration of mAbs with reduced agitation of the mAbs and infusate, as compared to administration by drip IV. The reduced agitation can help avoid problems due to mAbs instability, aggregation, and protein unfolding, potentially improving efficacy.

In certain embodiments, the infusion device comprises an elastomeric (e.g., ball) pump, wherein the pump comprises the receptacle containing the volume of solution, and wherein the tubing line or lines fluidly connect (e.g., directly or indirectly) the pump (and, therefore, the receptacle containing the volume of solution) to the patient via the above-described disposable infusion set, for intravenous delivery of the volume of solution to the patient.

The infusion device/system may include an intravenous (IV) bag or other receptacle containing a volume of drug solution to be administered to the patient. Elements of the infusion device are connected by tubing lines of a disposable set designed for one-time use. The drug solution is drawn from the IV bag or other receptacle with a pump (e.g., an elastomeric (e.g., ball) pump, a roller pump, or a centrifugal pump). The infusion device may optionally include a heater or other temperature control device. Additionally or alternatively, the infusion device may optionally include one or more of a rate control device (e.g., a pressure-regulating valve, a pressure responsive valve, or the like), one or more sensors, and/or feedback circuitry. The heating element may alternatively or additionally include an air venting mechanism. In certain embodiments, the air venting mechanism is part of the filter (e.g., inline filter).

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for administering an antibody treatment via an infusion device, the method comprising:
    administering to a patient by intravenous infusion, using the infusion device, a volume of solution comprising one or more members of the group consisting of (i) to (iv) as follows: (i) one or more monoclonal and/or polyclonal antibodies (mAbs and/or pAbs), (ii) one or more antibody drug conjugates (ADCs), (iii) one or more lipid drug conjugates (LDCs), and (iv) intravenous immunoglobulin (IVIg), wherein
    the infusion device comprises a pump and a disposable infusion set comprising a tubing line or lines and a filter, wherein the filter comprises a filter membrane material that provides negligible binding of the one or more antibodies to the filter membrane, wherein the tubing line or lines fluidly connect (a) an intravenous (IV) bag or other receptacle containing the volume of solution to the pump and/or (b) the pump to the patient, for intravenous delivery of the volume of solution to the patient, wherein:
    the pump administers the volume of solution at a dosing rate of at least 35 mg of the one or more antibodies per minute and at a total antibody concentration of less than or equal to 20 mg/mL.

2. The method of claim 1, wherein the volume of solution comprises an antibody treatment for the treatment of one or more members selected from the group consisting of cancer, a neurological disease, psoriasis, a respiratory disease, macular degeneration, cytokine release syndrome, Castelman disease, a disease caused by a pathogen, an organ transplant, and a tissue transplant.

3. The method of claim 1, wherein the volume of solution comprises one or more antibody drug conjugates (ADCs) selected from the group consisting of ado-trastuzumab emtansine, brentuximab vedotin, inotuzumab ozogamicin, gemtuzumab ozogamicin, Moxetumomab pasudotox, polatuzumab vedotin-piiq, Enfortumab vedotin, Sacituzumab govitecan, Trastuzumab deruxtecan, belantamab mafodotin-blmf, loncastuximab tesirine-lpyl, and tisotumab vedotin-tftv.

4. The method of claim 1, wherein the volume of solution comprises an intravenous immunoglobulin (IVIg).

5. The method of claim 1, wherein the pump is capable of administering the volume of solution to the patient at an infusion rate of at least 30 mL/min.

6. The method of claim 1, wherein the pump is capable of administering the volume of solution to the patient at an infusion rate of at least 100 mL/min.

7. The method of claim 1, wherein administration of the volume of solution to the patient is completed in no more than 30 minutes.

8. The method of claim 1, wherein the one or more polyclonal and/or monoclonal antibodies comprises one or more members selected from the group consisting of: pembrolizumab, nivolumab, bevacizumab, ocrelizumab, rituximab, daratumumab, pertuzumab, trastuzumab, infliximab, tocilizumab, atezolizumab, tositumomab-1131, olaratumab, MabThera, basiliximab, ibritumomab tiuxetan, cetuximab, natalizumab, panitumumab, ranibizumab, eculizumab, ofatumumab, belimumab, ipilimumab, raxibacumab, obinutuzumab, siltuximab, ramucirumab, vedolizumab, alemtuzumab, necitumumab, dinutuximab, elotuzumab, reslizumab, bezlotoxumab, obiltoxaximab, avelumab, durvalumab, aducanumab, gantenerumab, donanemab, BAN2401, gosuranemab, zagotenemab, tilavonemab, semorinemab, cinpanemab, MEDI1341, domagrozumab, ofatumumab, inebilizumab, erenumab, fremanezumab, eptinezumab, galcanezumab, satralizumab, ravulizumab, aquaporumab, rozanolixizumab, nipocalimab, batoclimab, efgartigimod, rilotumumab, anti-thymocyte globulin [rabbit], lymphocyte immune globulin, anti-thymocyte globulin [equine] sterile solution, alemtuzumab, alpha-1 antitrypsin, and a double antibody conjugate that is an anti-CD3 and anti-CD7 agent.

9. The method of claim 1 wherein the pump is capable of administering the volume of solution to the patient at a volume of at least 10 mL/min.

10. The method of claim 1, wherein the pump is capable of administering the volume of solution to the patient at a volume of at least 15 mL/min.

11. The method of claim 1, wherein the filter membrane material comprises polyethersulfone (PES).

12. The method of claim 1, wherein the filter membrane material comprises cellulose acetate.

13. The method of claim 1, wherein the filter membrane material comprises regenerated cellulose acetate.

14. The method of claim 1, wherein the filter membrane material comprises nylon.

15. The method of claim 1, wherein the filter has pore size below 170 μm.

16. The method of claim 1, wherein the filter has pore size below 10 μm.

17. The method of claim 1, wherein the filter has pore size below 2 μm.

18. The method of claim 1, wherein the filter has pore size 0.2 μm.

* * * * *

UNITED STATES PATENT AND TRADEMARK OFFICE
CERTIFICATE OF CORRECTION

| | |
|---|---|
| PATENT NO. | : 11,806,507 B2 |
| APPLICATION NO. | : 17/840423 |
| DATED | : November 7, 2023 |
| INVENTOR(S) | : Regina E. Herzlinger |

It is certified that error appears in the above-identified patent and that said Letters Patent is hereby corrected as shown below:

In the Claims

At Column 16, Claim number 8, Line number 39, the word "MabThera" should be deleted.

Signed and Sealed this
Ninth Day of January, 2024

Katherine Kelly Vidal
*Director of the United States Patent and Trademark Office*